(12) United States Patent
Reiter et al.

(10) Patent No.: US 6,787,021 B2
(45) Date of Patent: Sep. 7, 2004

(54) PURIFICATION OF ONIUM HYDROXIDES BY ELECTRODIALYSIS

(75) Inventors: Robert J. Reiter, Austin, TX (US); Kelly Hefner, Del Valle, TX (US)

(73) Assignee: Sachem, Inc., Austin, TX (US)

(*) Notice: Subject to any disclaimer, the term of this patent is extended or adjusted under 35 U.S.C. 154(b) by 214 days.

(21) Appl. No.: 10/038,537

(22) Filed: Jan. 3, 2002

(65) Prior Publication Data

US 2003/0121787 A1 Jul. 3, 2003

(51) Int. Cl.[7] .............................................. B01D 61/44
(52) U.S. Cl. ..................... 205/746; 205/748; 205/688; 204/522; 204/537
(58) Field of Search ......................... 205/746, 748, 205/688; 204/522, 537

(56) References Cited

U.S. PATENT DOCUMENTS

| | | | |
|---|---|---|---|
| 4,714,530 A | 12/1987 | Hale et al. | 204/131 |
| 4,938,854 A | 7/1990 | Sharifian et al. | 204/130 |
| 5,439,564 A | 8/1995 | Shimizu et al. | 204/102 |
| 5,545,309 A | 8/1996 | Shimizu et al. | 205/437 |
| 5,709,789 A | 1/1998 | Shay et al. | 205/437 |
| 5,709,790 A | 1/1998 | Sharifian et al. | 205/437 |
| 5,753,097 A | 5/1998 | Sharifian et al. | 205/437 |
| 5,833,832 A * | 11/1998 | Shay et al. | 205/413 |
| 5,853,555 A | 12/1998 | Sharifian et al. | 204/537 |
| 5,868,916 A | 2/1999 | Moulton | 204/541 |
| 5,910,237 A | 6/1999 | Moulton et al. | 204/541 |
| 5,951,845 A | 9/1999 | Moulton | 205/746 |
| 5,959,845 A | 9/1999 | Faucher | 361/777 |
| 5,968,338 A * | 10/1999 | Hulme et al. | 205/703 |
| 6,207,039 B1 | 3/2001 | Moulton et al. | 205/703 |
| 6,217,743 B1 * | 4/2001 | Moulton et al. | 205/746 |

FOREIGN PATENT DOCUMENTS

JP 60-131985 7/1985

* cited by examiner

*Primary Examiner*—Arun S. Phasge
(74) *Attorney, Agent, or Firm*—Renner, Otto, Boisselle & Sklar, LLP (57) ABSTRACT

This invention relates to a process for improving the purity of an aqueous onium hydroxide solution. In particular, the invention relates to a process for improving the purity of aqueous onium hydroxide solutions containing undesirable amounts of anions. The invention also relates to the improved high purity onium hydroxide solutions obtained by the above method.

37 Claims, 1 Drawing Sheet

PURIFICATION OF ONIUM HYDROXIDES BY ELECTRODIALYSIS

TECHNICAL FIELD

This invention relates to a process for improving the purity of an aqueous onium hydroxide solution. In particular, the invention relates to a process for improving the purity of aqueous onium hydroxide solutions containing undesirable amounts of anions. The invention also relates to the improved high purity onium hydroxide solutions obtained by the above method.

BACKGROUND OF THE INVENTION

Onium hydroxides, such as quaternary ammonium hydroxides including tetramethylammonium hydroxide (TMAH) and tetraethylammonium hydroxide (TEAH), are strong organic bases that have been known for many years. Quaternary ammonium hydroxides have found a variety of uses including use in zeolite manufacture and polymer manufacture. Aqueous solutions of quaternary ammonium hydroxides, particularly TMAH solutions, have also been used extensively as a developer for photoresists in printed circuit board and microelectronic chip fabrication. For a variety of reasons, it is desirable to minimize the overall amount of developer used in printed circuit board and microelectronic chip fabrication. One way to minimize the overall amount of hydroxide developer is to reuse the waste developer. Reusing developer reduces the amount lost and decreases disposal problems.

Waste developer contains impurities including ionic impurities and nonionic impurities. Ionic impurities include various metal cations such as sodium, potassium, zinc, nickel, aluminum, copper and calcium; and anions such as halides, nitrates, nitrites, carbonates, carboxylates, sulfates. Nonionic impurities include photoresists, surfactants, amines and numerous other organic molecules. Waste developer also contains relatively low concentrations of the hydroxide developer. Accordingly, there remains a continuing need to effectively recover hydroxide developer in a useable form so that it may be reused thereby minimize the overall amount of developer used in printed circuit board and microelectronic chip fabrication.

U.S. Pat. No. 4,714,530 (Hale et al) describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

U.S. Pat. No. 4,938,854 (Sharifian et al) also describes an electrolytic process for purifying quaternary ammonium hydroxides by lowering the latent halide content. The electrolytic cell may be divided into an anolyte compartment and a catholyte compartment by a divider which may be an anion or cation selective membrane. The cathode in the catholyte compartment comprises zinc, cadmium, tin, lead, copper or titanium, or alloys thereof, mercury or mercury amalgam.

Japanese Kokai Patent No. 60-131985 (1985) (Takahashi et al) describes a method of manufacturing a high purity quaternary ammonium hydroxide in an electrolysis cell which is divided into an anode chamber and a cathode chamber by a cation exchange membrane. A quaternary ammonium hydroxide solution containing impurities is charged to the anode chamber and a direct current is supplied between two electrodes after water has been charged to the cathode chamber. Purified quaternary ammonium hydroxide is obtained from the cathode chamber. The purified quaternary ammonium hydroxide contains reduced amounts of alkali metals, alkaline earth metals, anions, etc.

U.S. Pat. Nos. 5,439,564 and 5,545,309 (Shimizu et al) relate to methods of processing waste liquid containing an organic quaternary ammonium hydroxide by contacting the waste liquid with a cation-exchanging material, eluting organic quaternary ammonium cations from the cation-exchanging material, and electrolyzing the eluate in a two chamber electrolytic cell equipped with an anode, cathode and cation-exchanging membrane. Organic quaternary ammonium hydroxide is obtained from the cathode chamber of the electrolytic cell.

U.S. Pat. No. 5,968,338 (Hulme et al) describes a process for regenerating onium hydroxides from solutions containing onium compounds such as hydroxides and salts using a cation exchange material, an acid to form a salt, and an electrochemical cell comprising at least three compartments to regenerate the onium hydroxide.

U.S. Pat. No. 6,207,039 (Moulton et al) describes a process for recovering an onium hydroxide or onium salt from a solution containing an onium compound (e.g., a hydroxide, salt, or mixture thereof) using an electrochemical cell comprising at least two compartments, a cathode, an anode, and a divider, wherein at least one compartment contains an ion exchange material. A variety of electrochemical cells are described. In one cell illustrated in FIG. 3, the cell comprises an anode, a cathode and a unit cell containing in sequence beginning at the anode, a first bipolar membrane, a cation selective membrane and a second bipolar membrane. The compartment formed by the first bipolar membrane and the cation exchange membrane (feed compartment) contains an ion exchange material.

Another electrochemical cell which is illustrated in FIGS. 8 and 8A of the '039 patent comprises an anode, a cathode, and a unit cell containing in sequence beginning at the anode, a first bipolar membrane, a first cation selective membrane, a second cation selective membrane, and a second bipolar membrane. The feed compartment in both embodiments contains an ion exchange material. In the embodiment of FIG. 8B, the feed compartment is formed by the first bipolar membrane and the first cation selective membrane.

SUMMARY OF THE INVENTION

In one embodiment, the present invention is a process for improving the purity of aqueous onium hydroxide solutions which comprises:

(A) providing an electrochemical cell comprising at least four compartments, said compartments being formed by a cathode, an anode, and in order from the anode to the cathode, a first bipolar membrane, a first cation selective membrane, and a second bipolar membrane, (B) charging the onium hydroxide solution to a feed compartment formed by the first bipolar membrane and the first cation selective membrane wherein the feed compartment is free of any ion exchange material, (C) passing a current through the cell, and (D) recovering a purified onium hydroxide solution from the recovery compartment formed by the first cation selective membrane and the second bipolar membrane.

In another embodiment, the present invention relates to a process for improving the purity of an aqueous onium hydroxide solution which comprises:

(A) providing an electrochemical cell comprising at least 5 compartments, said compartments being formed by an anode, a cathode, and in order from the anode to the cathode, a first bipolar membrane, a first cation selective membrane, a second cation selective membrane, and a second bipolar membrane, (B) charging the onium hydroxide solution to a feed compartment formed by the first bipolar membrane and the first cation selective membrane wherein the feed compartment is free of any ion exchange material, (C) passing a current through the cell, and (D) recovering a purified onium hydroxide from the recovery compartment formed by the second cation selective membrane and the second bipolar membrane.

The onium hydroxide solutions that can be purified by the processes of the invention include quaternary ammonium hydroxides, quaternary phosphonium hydroxides, and tertiary sulfonium hydroxides.

As a result of the process of the present invention, recycled solutions of onium hydroxides can be obtained in which the concentration and purity is increased. Recycling spent solutions of onium hydroxides provides not only cost savings, but also environmental benefits by eliminating or reducing the need for synthesizing new hydroxide compound solutions, the associated expensive purification processes, and the toxicity of waste solution effluents. In addition, it is not necessary to store large amounts of chemicals. The relatively high concentration and purity of the onium hydroxide solutions obtainable via the present invention can effectively be used in numerous applications where onium hydroxide solutions are required.

DESCRIPTION OF THE EMBODIMENTS

In accordance with the present invention, the purity of aqueous onium hydroxide solutions containing undesirable anions is improved via electrodialysis in an electrochemical cell. In one embodiment, aqueous solutions of onium hydroxides containing undesirable amounts of anions can be treated in accordance with the process of the invention to produce an onium hydroxide solution containing lesser amounts of the undesirable anions. Anions which may be present include halide, carbonate, formate, nitrite, nitrate, acetate, sulfate, etc. In one embodiment, the aqueous solutions of onium hydroxide which can be purified in accordance with the present invention are solutions obtained by eluting onium cations absorbed on a cation exchange material with an aqueous solution of an organic base such as described in copending patent application Ser. No. 09/693,293 filed Oct. 20, 2000.

As noted herein and in the claims, the feed compartments of the electrochemical cells are free of any ion exchange material. That is, the feed compartments do not contain any cation or anion exchange material of the types described in U.S. Pat. No. 6,207,039. In another embodiment, the other compartments of the electrochemical cells also are free of ion exchange material.

The onium hydroxides may generally be characterized by the formula $$A(OH)_x \tag{I}$$

wherein A is an onium group and x is an integer equal to the valence of A. Examples of onium groups include ammonium groups, phosphonium groups, and sulfonium groups. In one embodiment, the onium hydroxide should be sufficiently soluble in a solution such as water, alcohol or other organic liquid, or mixtures thereof to permit a useful recovery rate.

The quaternary ammonium hydroxides and quaternary phosphonium hydroxides may be characterized by the formula (II)

wherein A is a nitrogen or phosphorus atom, $R^1$, $R^2$, $R^3$ and $R^4$ are each independently alkyl group containing from 1 to about 20 carbon atoms, hydroxy alkyl or alkoxy alkyl group containing from 2 to about 20 carbon atoms, aryl groups, or hydroxy aryl groups, or $R_1$ and $R_2$ together with A may form a heterocyclic group provided that if the heterocyclic group contains a C=A group, $R^3$ is the second bond.

The alkyl groups $R^1$ to $R^4$ may be linear or branched, and specific examples of alkyl groups containing from 1 to 20 carbon atoms include methyl, ethyl, propyl, butyl, pentyl, hexyl, heptyl, octyl, isooctyl, nonyl, decyl, isodecyl, dodecyl, tridecyl, isotridecyl, hexadecyl and octadecyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. In one preferred embodiment, $R^1$, $R^2$, $R^3$ and $R^4$ are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

The quaternary a ammonium hydroxides which can be recycled or purified in accordance with the process of the present invention may be represented by Formula III (III)

wherein $R^1$, $R^2$, $R^3$ and $R^4$ are as defined in Formula II. In one preferred embodiment, $R^1$–$R^4$ are alkyl groups containing from 1 to about 4 carbon atoms and hydroxyalkyl groups containing 2 or 3 carbon atoms. Most often the quaternary ammonium hydroxides purified in accordance with the process of the invention will be tetramethylammonium hydroxide (TMAH) or tetraethylammonium hydroxide (TEAH). Specific examples of such ammonium hydroxides include tetramethylammonium hydroxide, tetraethylammonium hydroxide, tetrapropylammonium hydroxide, tetrabutylammonium hydroxide, tetra-n-octylammonium hydroxide, methyltriethylammonium hydroxide, diethyldimethylammonium, methyltripropylammonium hydroxide, methyltributylammonium hydroxide, cetyltrimethylammonium hydroxide, trimethylhydroxyethylammonium hydroxide, trimethylmethoxyethylammonium hydroxide, dimethyidihydroxyethylammonium hydroxide, methyltrihydroxyethylam-monium hydroxide, phenyltrimethylammonium hydroxide, phenyltriethylam-monium hydroxide, benzyltrimethylammonium hydroxide, benzyltriethylam-monium hydroxide, dimethylpyrolidinium hydroxide, dimethylpiperidinium hydroxide, diisopropylimidazolinium hydroxide, N-alkylpyridinium hydroxide, etc.

Examples of quaternary phosphonium hydroxides representative of Formula II wherein A=P which can be purified in accordance with the process of the present invention include tetramethylphosphonium hydroxide, tetraethylphosphonium hydroxide, tetrapropylphosphonium hydroxide, tetrabutylphosphonium hydroxide, trimethylhydroxyethylphosphonium hydroxide, dimethyldihydroxyethylphosphonium hydroxide, methyltrihy-droxyethylphosphonium hydroxide, phenyltrimethylphosphonium hydroxide, phenyltriethylphosphonium hydroxide and benzyltrimethylphosphonium hydroxide, etc.

In another embodiment, the tertiary sulfonium hydroxides which can be recycled or purified in accordance with this invention may be represented by the formula (IV)

wherein $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R^1$ and $R^2$ together with S may form a heterocyclic group provided that if the heterocyclic group contain a C=S group, $R^3$ is the second bond.

Examples of the tertiary sulfonium hydroxides represented by Formula IV include trimethylsulfonium hydroxide, triethylsulfonium hydroxide, tripropylsulfonium hydroxide, etc.

Onium hydroxides are commercially available. Additionally, onium hydroxides can be prepared from the corresponding onium salts such as the corresponding onium halides, carbonates, formates, sulfates and the like.

Various methods of preparation are described in U.S. Pat. Nos. 4,917,781 (Sharifian et al) and 5,286,354 (Bard et al) which are hereby incorporated by reference. There is no particular limit as to how the onium hydroxide solutions are obtained or prepared.

Prior to electrodialysis, the solutions containing the onium hydroxide and impurities may be optionally concentrated or otherwise pretreated. That is, the concentration of the onium hydroxide in the solution may be increased prior to electrodialysis and/or various impurities may be removed from the onium compound solution.

In some embodiments, it may be desirable to concentrate the solution of the onium hydroxide prior to electrodialysis. Concentration procedures are known to those skilled in the art and include evaporation, distillation, nanofiltration and reverse osmosis among others. Similarly, these concentration procedures may optionally be used to concentrate the onium hydroxide solution (further described below) charged to the feed compartment of an electrodialytic cell.

In other embodiments, it may be desirable to pretreat the solution of the onium hydroxide with some form of filtration prior to electrodialysis in accordance with the invention. Various types of filtration can be performed including gravity filtration, microfiltration such as nanofiltration, cross-flow filtration, cartridge filtration, vacuum filtration and pressure induced filtration. Related straining and screening pretreatments may also be performed. Filter membranes can be made of known materials useful for separating solids from liquids including plastics such as PTFE, PVDF, PET, nylons, polyethylene and polypropylene, cellulose acetate, cellulose nitrate, regenerated cellulose, nitrocellulose, paper including ashless paper, various fibers including glass fibers, and various particulates including activated carbon, silica, sand, etc. Alternatively, pretreatment can involve contacting the solution of the onium hydroxide with various particulate materials, for example activated carbon, so that organic impurities are adsorbed and thus from solution by the particulate material.

In some embodiments, more than one type (or pass) of a filtration pretreatment can be performed as each filtration pretreatment may remove a different species of impurity. For example, in one embodiment two filtration pretreatments are performed: organic impurities are substantially or partially removed by gravity filtration and metal impurities are substantially or partially removed by another pass of gravity filtration after increasing the pH of the solution causing certain metals to form insoluble hydroxide salts thereby facilitating filtration (and thus separation of the insoluble species).

In other embodiments, it may be desirable to pretreat the solution of the onium hydroxide with some form of metal treatment prior to electrodialysis in accordance with the invention. A metal pretreatment removes excess metal impurities from the solution of the onium hydroxide. In one embodiment, metal pretreatment involves contacting a solution of the onium hydroxide with a preliminary ion exchange material for metal removal. The preliminary ion exchange material is preferably a preliminary cation exchange material which can selectively discriminate between metal cations and onium cations so that at least a portion of metal ion impurities in the solution of the onium compound is adsorbed by the preliminary ion exchange material. For example, a preliminary ion exchange material, for which sodium has an affinity, can be used as a metal pretreatment to remove sodium from the solution of the onium hydroxide prior to electrodialysis in accordance with the invention.

In another embodiment, metal pretreatment involves contacting a solution of the onium hydroxide with a metal complexing compound. Metal complexing compounds adsorb, bond to, complex, coordinate, chelate or otherwise engage at least a portion of the metal ion impurities in the solution of the onium compound thereby removing them prior to contact with the cation exchange material in accordance with the invention. Examples of metal complexing compounds include crown ethers, cryptands and chelating compounds (diamines, diketonates, etc).

In yet another embodiment, metal pretreatment may involve contacting a solution of the onium compound with an acid or salt capable of forming an insoluble precipitate (at least partially insoluble) with a metal cation thereby enabling easy removal of the precipitate and thus the metal from electrodialysis in accordance with the invention.

The electrochemical cells useful in the present invention contain at least an anode and a cathode, first and second bipolar membranes, and one or more cation selective membranes between the two bipolar membranes. There may be one or more unit cells assembled for operational positioning between the anode and the cathode. Electrochemical cells containing various unit cells and multiple unit cells are described herein which are useful in the process of the present invention. Multiple unit cells may be defined by a number of compartments between an anode and a cathode, or multiple unit cells may be defined by a number of compartments including an anode and a cathode. There is no particular limit to the number of unit cells which can be used. Nevertheless, in one embodiment, electrochemical cells which are useful according to the present invention may contain from 1 to about 25 unit cells, preferably from about 1 to about 10 unit cells.

The electrochemical cells useful in the present invention contain at least four or five compartments. Electrochemical cells containing at least four compartments generally have two electrode rinse or buffer compartments, a feed compartment and a recovery compartment. Electrochemical cells containing at least five compartments generally have a feed compartment, a recovery compartment, two electrode rinse or buffer compartments, and a pass or intermediate compartment between the feed compartment and the recovery compartment.

Ionic solutions or electrolytes are charged to one or more compartment of the electrodialytic cell. The solution may be aqueous based, alcohol or glycol based, another organic solution, or combinations thereof. In other words, the solutions may contain water, mixtures of water and an organic liquid, or an organic liquid where the organic liquids include alcohol such as methanol and ethanol, glycols, etc. In one embodiment, the solution charged to each compartment is an aqueous solution.

The concentration of the onium hydroxide initially charged into the feed compartment is in the range from about 0.1 M to about 6 M. In a preferred embodiment, the concentration of the onium salt in the solution charged into the feed compartment is from about 0.5 M to about 2 M. In electrochemical cells containing two or more feed compartments, the concentrations of the onium hydroxide in the solutions charged into the feed compartments may be the same or different for each feed compartment. The feed compartment, as the term implies, initially holds the onium hydroxide solution containing onium cations and undesirable anion which is to be purified by the present invention.

The recovery compartment initially is charged with a solution, and preferably an aqueous solution. The solution charged to the recovery compartment may or may not contain an ionic compound. An ionic compound is a chemical compound that partially or completely ionizes in solution, such as an electrolyte. In one embodiment, the ionic compound in the recovery compartment is the same as the onium hydroxide charged into the feed compartment (or the same as the onium hydroxide recovered from the recovery compartment). After passing a current through the cell, the onium hydroxide may be recovered or otherwise obtained from the recovery compartment at a certain concentration. In one embodiment, the concentration of the onium hydroxide in the recovery compartment is above about 0.5 M. In another embodiment, the concentration of the onium hydroxide in the recovery compartment is above about 1 M. In yet another embodiment, the concentration of the onium hydroxide in the recovery compartment is above about 2 M. In electrochemical cells containing two or more recovery compartments, the concentrations of the organic hydroxide in the solutions recovered from the recovery compartments may be the same or different for each recovery compartment.

The electrode rinse or buffer compartments (i.e., the compartments adjacent to the anode and cathode), contain a solution of an ionic compound at a certain concentration. The ionic compound serves to maintain conductivity and enable lower operating cell voltages. The concentration of the ionic compound in the solution charged into the electrode rinse compartments is in the range from about 0.1 M to about 5 M. In another embodiment, the concentration is from about 0.5 M to about 2 M. And in another embodiment, the concentration is from about 0.7 M to about 1.5 M. In electrochemical cells containing two or more electrode rinse compartments, the concentrations of the ionic compound in the solutions charged into the electrode rinse compartments may be the same or different for each compartment.

The intermediate or pass compartment, if present, initially is charged with a solution and preferably an aqueous solution. The solution charged to the intermediate pass compartment may or may not contain an ionic compound. The ionic compound, if present, may be the same or different from the ionic compound of the other compartments. The intermediate or pass compartment is defined by two cation exchange membranes. When the current is passed through the electrochemical cell, the onium cation passes from the feed compartment through the intermediate or pass compartment into the recovery compartment. Since most undesirable impurities do not pass through the intermediate or pass compartment, the pass compartment serves to further purify the resultant onium hydroxide.

Accordingly, in one embodiment, the process of the present invention comprises:

(A) providing an electrochemical cell comprising at least four compartments, said compartments being formed by a cathode, an anode, and in order from the anode to the cathode, a first bipolar membrane, a first cation selective membrane, and a second bipolar membrane, (B) charging the onium hydroxide solution to a feed compartment formed by the first bipolar membrane and the first cation selective membrane wherein the feed compartment is free of any ion exchange material, (C) passing a current through the cell, and (D) recovering a purified onium hydroxide solution from the recovery compartment formed by the first cation selective membrane and the second bipolar membrane.

Several embodiments of electrodialytic cells which may be used in the process of the present invention will be described in reference to the figures. Although numerous embodiments of the various electrodialytic cells are described in the figures, it would be readily apparent to those skilled in the art that additional numerous embodiments not specifically described in the figures exist within the scope of the invention.

Figure 1:
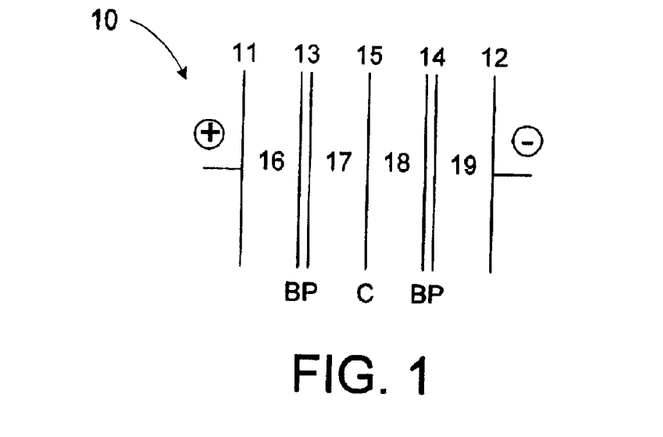
FIG. 1 is a schematic representation of a four compartment electrochemical cell containing one unit cell in accordance with the present invention.

An embodiment of an electrolytic cell comprising at least four compartments which is useful in the above process is illustrated in FIG. 1 which is a schematic representation of an electrochemical cell 10 containing an anode 11, a cathode 12, and a unit cell containing in sequence, beginning at the anode 11, a first bipolar membrane 13, a cation selective membrane 15, and a second bipolar membrane 14. This electrochemical cell 10 contains 4 compartments: namely, a first electrode rinse or buffer compartment 16, a feed compartment 17, a recovery compartment 18, and a second electrode rinse or buffer compartment 19.

In operation of the cell 10 illustrated in FIG. 1, an onium hydroxide feed solution containing a quantity of anion impurities is charged to the feed compartment 17. A solution, preferably an aqueous solution, of an ionic compound (electrolyte) is charged to the first and second electrode rinse or buffer compartments 16 and 19 and the recovery compartment 18. An electrical potential is established and maintained between the anode and the cathode to produce a flow or current across the cell whereupon the anions present in the feed solution remain in the feed compartment 17. The onium cation is attracted toward the cathode 12 and passes through the cation selective membrane 15 into the recovery compartment 18 where it combines with the hydroxide ions formed on the surface of the anode side of the second bipolar membrane 14 to produce the desired onium hydroxide. Impurities are not attracted to the cathode and/or do not pass through the cation selected membrane 15 and thus remain in the feed compartment 17. The onium hydroxide is formed in and recovered from the recovery compartment 18.

In another embodiment of the present invention, the process for improving the purity of an aqueous onium hydroxide solution utilizes an electrochemical cell comprising at least 5 compartments. The process comprises:
(A) providing an electrochemical cell comprising at least 5 compartments, said compartments being formed by an anode, a cathode, and in order from the anode to the cathode, a first bipolar membrane, a first cation selective membrane, a second cation selective membrane, and a second bipolar membrane,
(B) charging the onium hydroxide solution to a feed compartment formed by the first bipolar membrane and the first cation selective membrane wherein the feed compartment is free of any ion exchange material,
(C) passing a current through the cell, and
(D) recovering a purified onium hydroxide from the recovery compartment formed by the second cation selective membrane and the second bipolar membrane.

Figure 2:
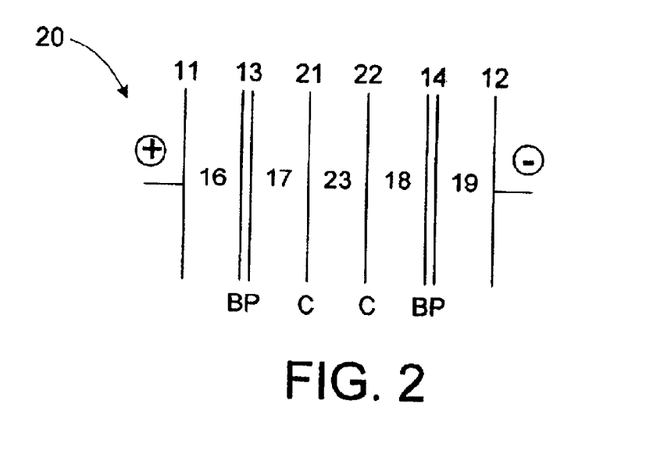
FIG. 2 is a schematic representation of a five compartment electrochemical cell in accordance with the present invention.
Figure 3:
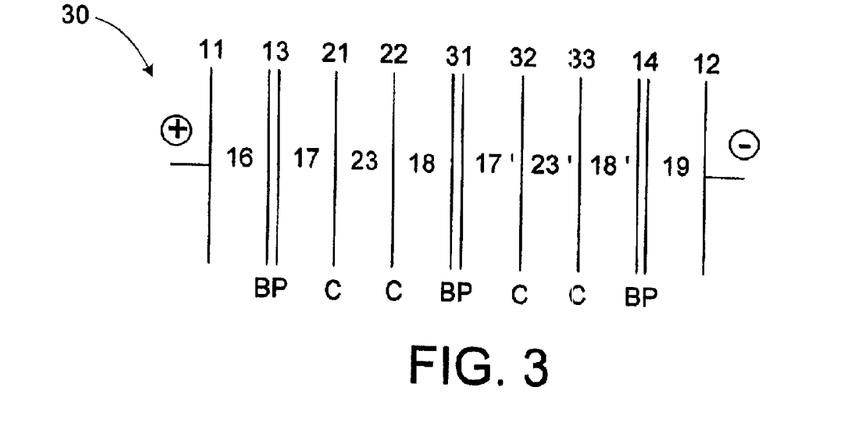
FIG. 3 is a schematic representation of an eight compartment electrochemical cell in accordance with the present invention.

Electrochemical cells utilized in this embodiment are illustrated in FIGS. 2 and 3. FIG. 2 is a schematic representation of an electrochemical cell 20 containing an anode 11, a cathode 12, and a unit cell containing in sequence beginning at the anode 11, a first bipolar membrane 13, a first cation selective membrane 21, a second cation selective membrane 22, and a second bipolar membrane 14. Thus, the electrodialytic cell 20 contains five compartments: a first electrode rinse or buffer compartment 16, a feed compartment 17, an intermediate or pass compartment 23, a recovery compartment 18, and a second electrode rinse or buffer compartment 19.

In operation of the electrodialytic cell 20 illustrated in FIG. 2, an onium hydroxide solution is charged to the feed compartment 17. An electrolyte is charged to the first and second electrode rinse compartments 16 and 19, the pass compartment 23 and the recovery compartment 18. In one embodiment, the electrolyte charged to these compartments is an aqueous solution containing the same onium hydroxide as charged to the feed compartment, but which does not contain significant amounts of impurities such as anions. An electrical potential is established and maintained between the anode and the cathode to produce a flow or current across the cell whereupon any anions contained in the onium hydroxide solution charged to the feed compartment 17 remain in the feed compartment 17. The onium cation is attracted toward the cathode 12 and passes through the first cation selective membrane 21 into the intermediate compartment 23 and thereafter through the second cation selective membrane 22 into the recovery compartment 18 where it combines with hydroxide ions formed on a surface of the anode side of the second bipolar membrane 14 to produce the desired onium hydroxide. Impurities are not attracted to the cathode 12 and/or do not pass through the first cation selective membrane 22, and thus remain in the feed compartment 17. The regenerated onium hydroxide is recovered from the recovery compartment 18.

Another embodiment of an electrochemical cell which is useful in the process of the present invention is illustrated in FIG. 3 which is a schematic representation of an electrochemical cell 30 containing eight compartments. This embodiment is an illustration of an electrodialytic cell containing two of the unit cells utilized in the embodiment of FIG. 2, the units being separated by a third bipolar membrane 31. Accordingly, the electrodialytic cell 30 illustrated in FIG. 3 contains an anode 11, a cathode 12, a first unit cell containing in sequence beginning at the anode 11, a first bipolar membrane 13, a first cation selective membrane 21, a second cation selective membrane 22 in a third bipolar membrane 31, a second unit cell comprising the third bipolar membrane 31, a third cation selective membrane 32, a fourth cation selective membrane 33 and a second bipolar membrane 14. Accordingly, this cell 30 contains eight compartments: a first electrode rinse compartment 16, a first feed compartment 17, a first intermediate or pass compartment 23, a first recovery compartment 18, a second feed compartment 17', a second intermediate or pass compartment 23', a second recovery compartment 18' and a second electrode rinse compartment 19.

In operation of the electrochemical cell 30 illustrated in FIG. 3, an onium hydroxide solution containing anion impurities is charged to the feed compartments 17 and 17'. An electrolyte is charged to the first and second electrode rinse compartments 16 and 19, the first and second intermediate compartments 23 and 23', and the first and second recovery compartments 18 and 18'. An electrical potential is established and maintained between in the anode and the cathode to produce a flow or current across the cell whereupon the onium cations in each of the feed compartments 17 and 17' are attracted to the cathode 12. Thus, the onium cation in compartment 17 passes through first intermediate compartment 23 into recovery compartment 18 where the cation combines with hydroxide ions to produce the desired onium hydroxide in the recovery compartment 18. Similarly, the onium cations in second feed compartment 17' pass through the third cation selective membrane 32 into the second intermediate compartment 23' and thereafter through the fourth cation selective membrane 33 into the second recovery compartment 18' where the cations combine with hydroxide ions to form the desired onium hydroxide which can be recovered from the second recovery compartment 18'. Since any anions present in the onium hydroxide solutions charged to the feed compartments 17 and 17' are not passed through the cation selective membranes, the onium hydroxide solutions recovered from the recovery compartments 18 and 18' contain a reduced amount of the undesirable anions.

Operation of the process of the present invention may be continuous or batchwise. Operation of the process of the present invention generally is continuous and certain components are continuously recirculated. Circulation is effected by pumping and/or by gas evolution.

Various materials can be used as anodes in the electrochemical cells. For example, the anode may be made of metals such as titanium-coated electrodes, tantalum, nickel, zirconium, hafnium or alloys of the same. Generally, the anodes will have a non-passivable and catalytic film which may comprise metallic noble metals such as platinum, iridium, rhodium or alloys thereof, or a mixture of electro-conductive oxides containing at least one oxide or mixed oxides of a noble metal such as platinum, iridium, ruthenium, palladium or rhodium. In one embodiment, the anode is a dimensionally stable anode such as an anode having a titanium base with ruthenium and/or iridium oxides thereon. In another embodiment, the anode is made of titanium coated with platinum.

Various materials which have been used as cathodes in electrochemical cells can be included in the cathodes is used in the above and other embodiments of the present invention. Cathode materials include nickel, iron, stainless steel, nickel plated titanium, graphite, carbon steel (iron) or alloys thereof etc. The term "alloy" is used in a broad sense and includes intimate mixtures of two or more metals as well as one metal coated onto another metal.

The cation selective membranes used in the cells and the process of the invention may be any of those which have been used in the electrochemical purification or recycling of onium hydroxides. In one embodiment the cation selective membranes contain a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid, perfluorocarboxylic acid, and perfluorosulfonic and/perfluorocarboxylic acid, perfluorocarbon polymer membranes such as sold by the E. I. dupont Nemours & Co. under the general trade designation "Nafion" such as DuPont's Cationic Nafion 902 membrane. Other suitable cation selective membranes include CMV cation selective membranes from Asahi Glass and styrene-diviniyl benzene copolymer membranes containing cation selective groups such as sulfonate groups, carboxylate groups, etc. Raipore Cationic R1010, (from Pall RAI), and NEOSEPTA CMH and NEOSEPTA CM1 membranes from Tokuyama Soda are useful particularly with the higher molecular quaternary compounds. A perfluorocarboxylic acid cation selective membrane useful in the invention is available from Asahi glass under the designation F795. The preparation and structure of cation selective membranes is described in the chapter entitled "Membrane Technology" in Encyclopedia of Chemical Technology, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

The bipolar membranes used in the electrochemical cells are composite membranes containing three parts: a cation selective side or region, an anion selective side or region, and an interface between the two regions. When a direct current passes across a bipolar membrane, with the cation selective side toward or facing the cathode, electrical conduction is achieved by the transport of H+ and OH– ions which are produced by the dissociation of water which occurs at the interface under the influence of an electrical field.

Bipolar membranes are described, for example, in U.S. Pat. Nos. 2,829,095, 4,024,043 (single film bipolar membranes) and in U.S. Pat. No. 4,116,889 (cast bipolar membranes). The bipolar membranes useful in the process of the present invention include NEOSEPTA BIPOLAR 1 by Tokuyama Soda, WSI BIPOLAR, and Aqualytics Bipolar membranes.

Electrodialysis is conducted by applying a current (generally direct current) between the anode and the cathode. The current which is passed through the cell is a current dictated by the design and performance characteristics of the cell, which are readily apparent to those skilled in the art and/or can be determined by routine experimentation. Current densities between about 10 and about 500 milliamps per square centimeter may be used, and current densities between about 70 and about 300 milliamps per square centimeter are preferred. Higher or lower current densities can be used for certain specific applications. The current density is applied to the cell for a period of time which is sufficient to result in the regeneration or formation of the desired amount or concentration of the onium hydroxide in the recovery compartment.

During electrodialysis it is generally desirable that the temperature of the liquids within the cell be maintained within the range of from about 2° C. to about 90° C., and preferably from about 20° C. to about 60° C.

Although not wishing to be bound by any theory, operation of the electrochemical cells according to the invention is believed to be based, in part, on the migration of the cation of the onium hydroxide, initially charged in the feed compartment, to the recovery compartment as a result of the current applied.

The following examples illustrate the processes of the present invention. Unless otherwise noted in the following examples and elsewhere in the specification and claims, all parts and percentages are by weight, all temperatures are in degrees centigrade, and pressure is at or near atmospheric pressure.

EXAMPLE 1

An electrodialysis cell is assembled according to FIG. 1 with the anode 11 comprising titanium coated with ruthenium oxide, and the cathode 12 comprising stainless steel. The first and second bipolar membranes 13 and 14 are NEOSEPTA BIPOLAR-1 by Tokuyama Soda. The cation selective membrane 15 is a Nafion 90209 cation selective membrane from DuPont. The electrode rinse compartments 16 and 19 are charged with a 0.5 M tetramethyl ammonium hydroxide solution, and the feed compartment 17 is charged with a 1.0 M tetramethyl ammonium hydroxide solution that contains about 194 ppm chloride. The recovery compartment 18 is charged with a 1.6 M aqueous solution of tetramethyl ammonium hydroxide. After all of the compartments have been charged as described, electrodialysis is carried out at a current density of 40 mamp/cm$^2$ for about 22 hours. A 2.0 M tetramethyl ammonium hydroxide solution is recovered from the recovery compartment 18, and the recovered solution has a chloride content of 1.6 ppm.

EXAMPLE 2

An electrodialysis cell is assembled according to FIG. 3 with the anode comprising titanium coated with platinum, and the cathode 12 comprising stainless steel. The first, second and third bipolar membranes (13, 14 and 31) utilized in this example are the same as those utilized in Example 1, and the cation selective membranes 21, 22, 32 and 33 are purchased from Asahi Glass Co. under the trade designation F795.

The electrode rinse compartments 16 and 19 are charged with a 0.5 M tetramethyl ammonium hydroxide solution. The first feed compartment 17 and the second feed compartment 17' are charged with a 1.6 M tetramethyl ammonium hydroxide solution containing 22 ppm chloride. The intermediate compartments 23 and 23' are charged with a 1.0 M tetramethyl ammonium hydroxide solution, and the first and second recovery compartments (18 and 18') are charged with a 2.2 M tetramethyl ammonium hydroxide solution. After all of the compartments are charged as described above, electrodialysis is carried out initially at a current density of 70 mamp/cm². As the electrodialysis continues for 68 hours, the recirculating feed solution is allowed to deplete to 0.39 M. The solutions in the recovery compartments 18 and 18' are combined and diluted with ultrapure deionized water to maintain a 2.2 M tetramethyl ammonium hydroxide solution with a chloride concentration below 100 ppb.

While the invention has been explained in relation to its embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for improving the purity of an aqueous onium hydroxide solution which comprises:
   (A) providing an electrochemical cell comprising at least four compartments, said compartments being formed by a cathode, an anode, and in order from the anode to the cathode, a first bipolar membrane, a first cation selective membrane, and a second bipolar membrane, wherein the compartment adjacent to the cathode is formed by the second bipolar membrane and the cathode,
   (B) charging the onium hydroxide solution to a feed compartment formed by the first bipolar membrane and the first cation selective membrane, wherein the feed compartment is free of ion exchange material,
   (C) passing a current through the cell, and
   (D) recovering a purified onium hydroxide solution from the recovery compartment formed by the first cation selective membrane and the second bipolar membrane.

2. The process of claim 1 wherein the onium hydroxide is a quaternary ammonium hydroxide, a quaternary phosphonium hydroxide, or a tertiary sulfonium hydroxide.

3. The process of claim 1 wherein the onium hydroxide is a quaternary ammonium hydroxide.

4. The process of claim 3 wherein the quaternary ammonium hydroxide is characterized by the formula wherein $R^1$, $R^2$, $R^3$ and $R^4$ are each independently alkyl groups containing from 1 to about 10 carbon atoms, hydroxyalkyl or alkoxyalkyl groups containing 2 to about 10 carbon atoms, or aryl or hydroxyaryl groups, or $R^1$ and $R^2$ are alkyl groups which together with the nitrogen atom may form an aromatic or non-aromatic heterocyclic ring provided that if the heterocyclic group contains a —C=N—, $R^3$ is the second bond.

5. The process of claim 4 wherein $R^1$, $R^2$, $R^3$ and $R^4$ are alkyl groups containing from 1 to about 5 carbon atoms or hydroxy alkyl groups containing from 2 to about 5 carbon atoms.

6. The process of claim 4 wherein $R^1$, $R^2$, $R^3$ and $R^4$ are alkyl groups containing one or two carbon atoms.

7. The process of claim 1 wherein the cation selective membrane comprises a perfluorosulfonic acid, a perfluorocarboxylic acid, or a perfluorosulfonic acid-perfluorocarboxylic acid perfluoro hydrocarbon polymer membrane.

8. The process of claim 1 wherein an electrolyte is charged to the other compartments of the electrochemical cell.

9. The process of claim 8 wherein the electrolyte is an aqueous solution of the onium hydroxide.

10. The process of claim 1 wherein the onium hydroxide solution charged in step (B) contains a quantity of halide ions, and the solution recovered in step (D) contains a lesser quantity of halide ions.

11. A process for improving the purity of an aqueous onium hydroxide solution which comprises:
    (A) providing an electrochemical cell comprising at least 5 compartments, said compartments being formed by an anode, a cathode, and in order from the anode to the cathode, a first bipolar membrane, a first cation selective membrane, a second cation selective membrane, and a second bipolar membrane,
    (B) charging the onium hydroxide solution to a feed compartment formed by the first bipolar membrane and the first cation selective membrane, wherein the feed compartment is free of ion exchange material,
    (C) passing a current through the cell, and
    (D) recovering a purified onium hydroxide from the recovery compartment formed by the second cation selective membrane and the second bipolar membrane.

12. The process of claim 11 wherein the onium hydroxide is a quaternary ammonium hydroxide, a quaternary phosphonium hydroxide, or a tertiary sulfonium hydroxide.

13. The process of claim 11 wherein the onium hydroxide is a quaternary ammonium hydroxide.

14. The process of claim 13 wherein the quaternary ammonium hydroxide is characterized by the formula wherein $R^1$, $R^2$, $R^3$ and $R^4$ are each independently alkyl groups containing from 1 to about 10 carbon atoms, hydroxyalkyl or alkoxyalkyl groups containing 2 to about 10 carbon atoms, or aryl or hydro aryl groups, or $R^1$ and $R^2$ are alkyl groups which together with the nitrogen atom may form an aromatic or non-aromatic heterocyclic ring provided that if the heterocyclic group contains a —C=N—, $R^3$ is the second bond.

15. The process of claim 14 wherein $R^1$, $R^2$, $R^3$ and $R^4$ are alkyl groups containing from 1 to a out 5 carbon atoms or hydroxy alkyl groups containing from 2 to about 5 carbon atoms.

16. The process of claim 13 wherein $R^1$, $R^2$, $R^3$ and $R^4$ are alkyl groups containing from 1 or 2 carbon atoms.

17. The process of claim 11 wherein an electrolyte is charged to the other compartments of the electrochemical cell.

18. The process of claim 17 wherein the electrolyte is an aqueous solution of the onium hydroxide.

19. The process of claim 11 wherein the onium hydroxide solution charged in step (B) contains a quantity of halide ions, and the solution recovered in step (D) contains a lesser quantity of halide ions.

20. A process for reducing the halide content of an aqueous quaternary ammonium hydroxide solution containing halide ions which comprises:
(A) providing an electrochemical cell comprising at least four compartments, said compartment being formed by an anode, a cathode, and in order from the anode to the cathode a first bipolar membrane, a first cation selective membrane and a second bipolar membrane, wherein the compartment adjacent to the cathode is formed by the second bipolar membrane and the cathode,
(B) charging the quaternary ammonium hydroxide solution containing a quantity of halide ion to a feed compartment formed by the first bipolar membrane and the first cation selective membrane, wherein the feed compartment is free of ion exchange material,
(C) charging an electrolyte to the other compartments,
(D) passing a current through the cell, and
(E) recovering an aqueous quaternary ammonium hydroxide solution from the recovery compartment formed by the first cation selective membrane and the second bipolar membrane, wherein the quaternary ammonium hydroxide recovered from the recovery compartment contains less halide ion than the amount of halide ion present in the quaternary ammonium hydroxide solution charged to the feed compartment.

21. The process of claim 20 wherein the quaternary ammonium hydroxide is characterized by the formula wherein $R^1$, $R^2$, $R^3$ and $R^4$ are each independently alkyl groups containing from 1 to about 10 carbon atoms, hydroxyalkyl or alkoxyalkyl groups containing 2 to about 10 carbon atoms, or aryl or hydroxyaryl groups, or $R^1$ and $R^2$ are alkyl groups which together with the nitrogen atom may form an aromatic or non-aromatic heterocyclic ring provided that if the heterocyclic group contains a —C=N—, $R^3$ is the second bond.

22. The process of claim 21, wherein $R^1$, $R^2$, $R^3$ and $R^4$ are alkyl groups containing from 1 to about 5 carbon atoms or hydroxy alkyl groups containing from 2 to about 5 carbon atoms.

23. The process of claim 21 wherein $R^1$, $R^2$, $R^3$ and $R^4$ are methyl or ethyl groups.

24. The process of claim 20 wherein the electrolyte charged to the other compartment in step (C) is an aqueous solution of the quaternary ammonium hydroxide.

25. A process for reducing the halide content of an aqueous quaternary ammonium hydroxide solution containing halide ions which comprises:
(A) providing an electrochemical cell comprising at least 5 compartments containing water, said compartments being formed by an anode, a cathode, and in order from the node to the cathode, a first bipolar membrane, a first cation selective membrane, a second cation selective membrane, and a second bipolar membrane,
(B) charging the quaternary ammonium hydroxide solution containing a quantity of halide ion to a feed compartment formed by the first bipolar membrane and the first cation selective membrane, wherein the feed compartment is free of ion exchange material,
(C) charging an electrolyte to the other compartments,
(D) passing a current through the cell, and
(E) recovering a quaternary ammonium hydroxide solution from the recovery compartment formed by the second cation selective membrane and the second bipolar membrane, wherein the recovered quaternary ammonium hydroxide solution contains less halide ion than the amount of halide ion present in the quaternary ammonium hydroxide solution charged to the feed compartment in step B.

26. The process of claim 25 wherein the quaternary ammonium hydroxide is characterized by the formula wherein $R^1$, $R^2$, $R^3$ and $R^4$ are each independently alkyl groups containing from 1 to about 10 carbon atoms, hydroxyalkyl or alkoxyalkyl groups containing 2 to about 10 carbon atoms, or aryl or hydroxyaryl groups, or $R^1$ and $R^2$ are alkyl groups which together with the nitrogen atom may form an aromatic or non-aromatic heterocyclic ring provided that if the heterocyclic group contains a —C=N—, $R^3$ is the second bond.

27. The process of claim 26 wherein $R^1$, $R^2$, $R^3$ and $R^4$ are alkyl groups containing from 1 to about 5 carbon atoms, or hydroxy alkyl groups containing from 2 to about 5 carbon atoms.

28. The process of claim 26 wherein $R^1$, $R^2$, $R^3$ and $R^4$ are methyl or ethyl groups.

29. The process of claim 25 wherein the electrolyte charged to the other compartment in step (C) is an aqueous solution of the quaternary ammonium hydroxide.

30. A process for improving the purity of an aqueous onium hydroxide solution derived from the elution of onium cations absorbed on a cation exchange material with an aqueous solution of an inorganic base which comprises:
(A) providing an electrochemical cell comprising at least four compartments, said compartments being formed by a cathode, an anode, and in order from the anode to the cathode, a first bipolar membrane, a first cation selective membrane, and a second bipolar membrane, wherein the compartment adjacent to the cathode is formed by the second bipolar membrane and the cathode,
(B) charging the onium hydroxide solution to a feed compartment formed by the first bipolar membrane and the first cation selective membrane, wherein the feed compartment is free of ion exchange material,
(C) passing a current through the cell, and
(D) recovering a purified onium hydroxide solution from the recovery compartment formed by the first cation selective membrane and the second bipolar membrane.

31. The process of claim 30 wherein the onium hydroxide is a quaternary ammonium hydroxide, a quaternary phosphonium hydroxide or a tertiary sulfonium hydroxide.

32. A process for improving the purity of an aqueous onium hydroxide solution which comprises:
(A) providing an electrochemical cell comprising at least 5 compartments, said compartments being formed by an anode, a cathode, and in order from the anode to the cathode, a first bipolar membrane, a first cation selective membrane, a second cation selective membrane, and a second bipolar membrane, (B) charging a onium hydroxide solution derived from the elution of onium salt absorbed on a cation exchange material with an aqueous solution of an inorganic base to a feed compartment formed by the first bipolar membrane and the first cation selective membrane, wherein the feed compartment is free of ion exchange material, (C) passing a current through the cell, and (D) recovering a purified onium hydroxide from the recovery compartment formed by the second cation selective membrane and the second bipolar membrane.

33. The process of claim 32 wherein the onium hydroxide is a quaternary ammonium hydroxide, a quaternary phosphonium hydroxide or a tertiary sulfonium hydroxide.

34. A process for reducing the halide content of an aqueous quaternary ammonium hydroxide solution containing halide ions which comprises:

(A) providing an electrochemical cell comprising at least four compartments, said compartments being formed by an anode, a cathode, and in order from the anode to the cathode, a first bipolar membrane, a first cation selective membrane and a second bipolar membrane, wherein the compartment adjacent to the cathode is formed by the second bipolar membrane and the cathode, (B) charging a quaternary ammonium hydroxide solution derived from the elution of quaternary ammonium cations absorbed on a cation exchange material with an aqueous solution of an inorganic base and containing a quantity of halide ion to a feed compartment formed by the first bipolar membrane and the first cation selective membrane, wherein the feed compartment is free of ion exchange material, (C) charging an electrolyte to the other compartments, (D) passing a current through the cell, and (E) recovering an aqueous quaternary ammonium hydroxide solution from the recovery compartment formed by the first cation selective membrane and the second bipolar membrane, wherein the quaternary ammonium hydroxide recovered from the recovery compartment contains less halide ion than the amount of halide ion present in the quaternary ammonium hydroxide solution charged to the feed compartment.

35. The process of claim 34 wherein the onium hydroxide is a quaternary ammonium hydroxide, a quaternary phosphonium hydroxide or a tertiary sulfonium hydroxide.

36. A process for reducing the halide content of an aqueous quaternary ammonium hydroxide solution containing halide ions which comprises:

(A) providing an electrochemical cell comprising at least 5 compartments containing water, said compartments being formed by an anode, a cathode, and in order from the anode to the cathode, a first bipolar membrane, a first cation selective membrane, a second cation selective membrane, and a second bipolar membrane, (B) charging a quaternary ammonium hydroxide solution derived from the elution of quaternary ammonium cations absorbed on a cation exchange material with an aqueous solution of an inorganic base and containing a quantity of halide ion to a feed compartment formed by the first bipolar membrane and the first cation selective membrane, wherein the feed compartment is free of ion exchange material, (C) charging an electrolyte to the other compartments, (D) passing a current through the cell, and (E) recovering a quaternary ammonium hydroxide solution from the recovery compartment formed by the second cation selective membrane and the second bipolar membrane, wherein the recovered quaternary ammonium hydroxide solution contains less halide ion than the amount of halide ion present in the quaternary ammonium hydroxide solution charged to the feed compartment in step B.

37. The process of claim 36 wherein the onium hydroxide is a quaternary ammonium hydroxide, a quaternary phosphonium hydroxide or a tertiary sulfonium hydroxide.

* * * * *